United States Patent [19]
Chin

[11] Patent Number: 5,571,172
[45] Date of Patent: Nov. 5, 1996

[54] METHOD AND APPARATUS FOR ENDOSCOPIC GRAFTING

[75] Inventor: Albert K. Chin, Palo Alto, Calif.

[73] Assignee: Origin Medsystems, Inc., Menlo Park, Calif.

[21] Appl. No.: 290,361

[22] Filed: Aug. 15, 1994

[51] Int. Cl.$^6$ ............................................. A61F 2/06
[52] U.S. Cl. .......................... 623/1; 623/66; 606/108; 606/194; 128/898
[58] Field of Search ............................. 623/1, 11–12, 623/66; 606/108, 191–192, 194, 198; 128/898

[56] References Cited

U.S. PATENT DOCUMENTS

| | | |
|---|---|---|
| 4,271,839 | 6/1981 | Fogarty et al. . |
| 4,318,410 | 3/1982 | Chin . |
| 4,479,497 | 10/1984 | Fogarty et al. . |
| 4,493,711 | 1/1985 | Chin et al. . |
| 4,526,175 | 7/1985 | Chin et al. . |
| 4,562,596 | 1/1986 | Kornberg .................... 623/1 |
| 4,606,347 | 8/1986 | Fogarty et al. . |
| 4,630,609 | 12/1986 | Chin . |
| 4,863,440 | 9/1989 | Chin . |
| 4,884,573 | 12/1989 | Wijay et al. . |
| 4,921,483 | 5/1990 | Wijay et al. . |
| 5,196,024 | 3/1993 | Barath .................... 606/194 |
| 5,246,452 | 9/1993 | Sinnott .................... 623/1 |
| 5,304,220 | 4/1994 | Maginot .................... 128/898 |
| 5,309,896 | 5/1994 | Moll et al. . |
| 5,346,484 | 9/1994 | van Lindert .................... 604/358 |

OTHER PUBLICATIONS

Session II, Advances in Peripheral Techniques I—Endoluminal Grafts, International Congress VII, Endovascular Interventions, On the Cutting Edge, Feb. 14, 1994.

Session IX, Advances in Peripheral Techniques II—Aneurysm Exclusion and Intraluminal Bypass, International Congress VII, Endovascular Interventions, On the Cutting Edge, Feb. 17, 1994.

"Blunt Tip Trocar and Sleeve", Origin Medsystems, Inc., Menlo Park, California, Oct. 1992.

D. C. Brewster, "Vascular Surgery: Principles and Technique", Appleton & Lange, 1989, pp. 237–250, 461–466.

Primary Examiner—John G. Weiss
Assistant Examiner—P. Zuttarelli
Attorney, Agent, or Firm—Albert C. Smith

[57] ABSTRACT

Method and apparatus for reconstructing target tissue by grafting uses a stabilizing balloon cannula having an endoscope for visualizing the placement of the graft during the procedure. The method and apparatus advances a sheathed graft to the target tissue, releases the graft at the target site, occludes the target tissue, deploys a graft stabilizing catheter, dissects a cavity outside the target tissue site, maintains the dissection site, and then secures the graft to the target tissue. Alternatively, the method and apparatus creates a cavity extending to the target tissue using an everting balloon cannula with an endoscope, maintains the dissection site, introduces the graft to the target site via the dissection site, and then secures the graft to the target tissue.

12 Claims, 13 Drawing Sheets

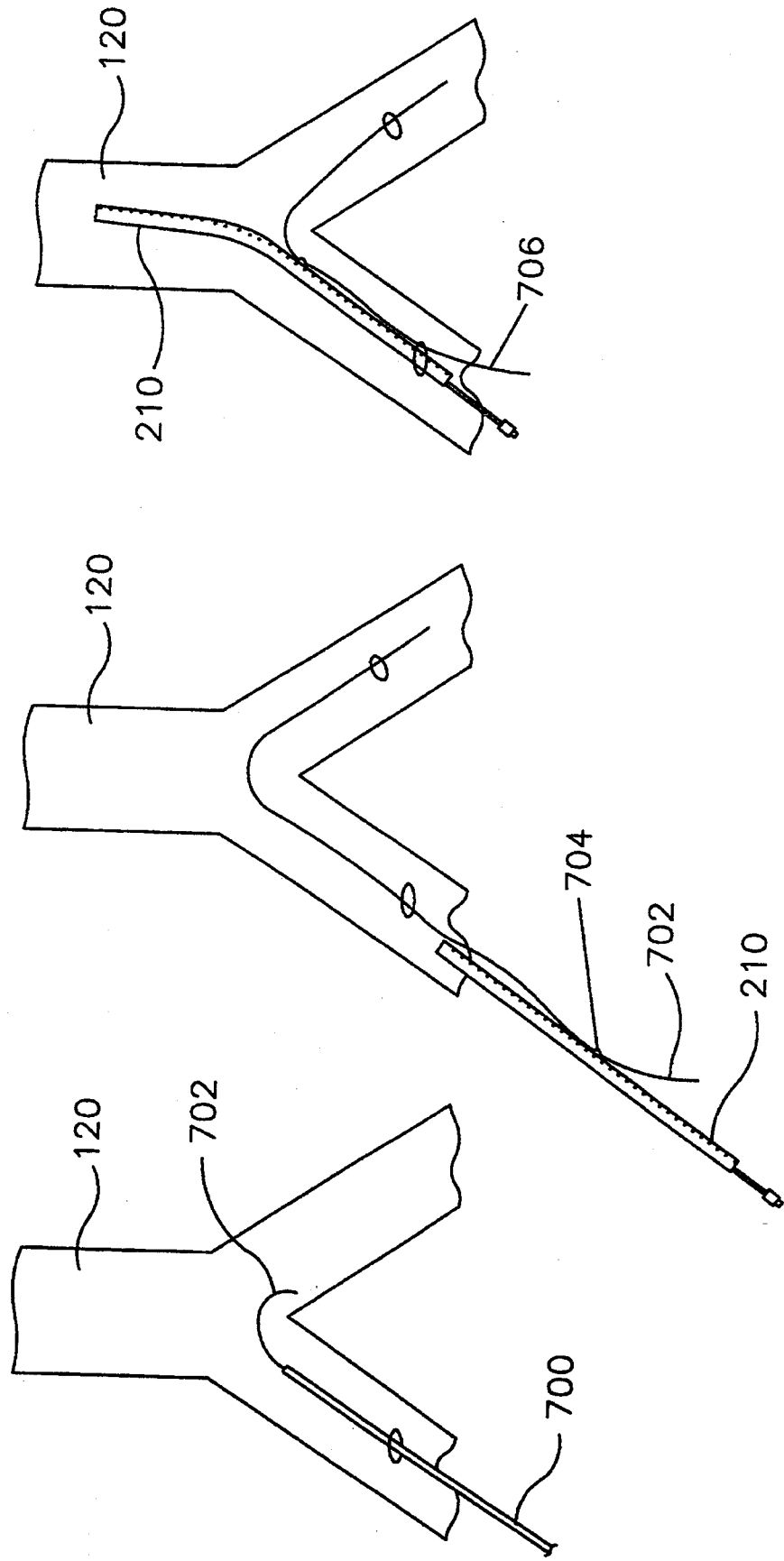

METHOD AND APPARATUS FOR ENDOSCOPIC GRAFTING

BACKGROUND OF THE INVENTION

1. Related Applications

This application is related to U.S. patent application Ser. No. 269,666, entitled "Everting Cannula Apparatus and Method", filed 1 Jul. 1994, the subject matter of which is incorporated herein by this reference.

2. Field of the Invention

The present invention relates generally to a method for grafting tissue at a target site, and specifically relates to endoscopic aortofemoral bypass grafting.

3. Description of Background Art

Prosthetic graft insertion from the abdominal aorta to the femoral vessels in the groin has become the standard method of direct surgical repair for aortoiliac occlusive disease over the past two decades. [See, Brewster, D.C., "Aortoiliac, Aortofemoral, and Iliofemoral Arteriosclerotic Occlusive Disease", in Haimovici, H. (ed.), *Vascular Surgery: Principles and Technique* (Appleton & Lange, 1989)]. The method is used in over 90% of such patients by most vascular surgeons. Present techniques for performing aortic reconstruction include open surgical bypass via an abdominal approach, a retroperitoneal approach, or infrequently, an endovascular approach, using a stented graft introduced through an incision in the femoral artery.

The open surgical approaches, either transabdominal or retroperitoneal, require large abdominal or flank incisions, approximately 20–30 cm in length for exposure and manipulation of the aorta. In this procedure, the aorta is cross-clamped for a period of time, which may increase the potential of ischemia to the kidneys or bowel. The postoperative recovery period is prolonged as a result of such trauma to the patient's organs and system. Laparoscopic approaches, using small incisions and rigid endoscopes to visualize inside the abdomen for the aortic anastomosis may be used and are known in the art. The laparoscopic technique requires multiple incisions, for example 4–5 incisions varying between 1–4 cm in length each. In addition, the laparoscopic technique requires multiple retractors to control and displace the bowel to enable access to the aorta. Aortic cross-clamping is required, and suturing the aortic anastomosis is difficult, increasing the cross-clamp time. The operative time is prolonged using this approach due to the difficulties associated with bowel retraction.

The most recent technique is the endovascular approach, which does not require abdominal incisions, since the graft is introduced via a groin incision and a femoral artery cutdown. Aortic cross-clamping is not required with this approach. The stented grafts used in practicing this technique are large in diameter, and graft introduction is only possible in patients with large, undiseased femoral arteries. Metal stents or anchors used to secure the proximal aortic end of the graft may not hold the graft properly, leading to graft migration. Alternatively, the metal stents or anchors may work their way through the wall of the aorta, causing aortic perforation and death.

Thus, there remains a need for a less invasive technique for performing aortofemoral bypass grafting that decreases the trauma to a patient's system and organs and the concomitant recovery time.

SUMMARY OF THE INVENTION

In accordance with the present invention, aortofemoral bypass grafting is performed using a specialized dissecting balloon cannula having an endoscope for visualizing the placement of the graft during the procedure.

In one embodiment of the present invention, a sheathed graft is advanced via a femoral cutdown. Once the graft is released from the sheath at the target location, such as at the aorta, a stabilizing system is advanced to the graft site. By separating the steps of graft insertion and graft stabilization at the target site, e.g., against the inside of the aorta, conventional insertion of a large diameter system through the femoral artery is avoided, and the technique of the present invention becomes applicable to a larger group of patients. Specifically, the contralateral femoral graft limb is pulled into position using a prior placed guidewire, and this avoids the difficulty commonly associated with the conventional technique of catching free ends of intravascular catheters using basket snares, and the like.

Once the graft is in position, a retroperitoneal space is created surrounding the aorta, using an everting dissection cannula. The space is maintained via retroperitoneal insufflation, or via a gasless technique incorporating mechanical retraction or structural balloon support. The aorta is isolated, and the proximal anastomosis is performed from the outside of the aorta, using interrupted suture anchors or a running suture. The aorta may be cross-clamped during the performance of the anastomosis, or an occlusion balloon may be advanced from the femoral access site.

In an alternative embodiment of the present invention, an everting balloon cannula is used to dissect a passageway from the infrarenal area to below the aortic bifurcation. A mechanical retraction system or a structural balloon then is used to maintain the retroperitoneal working cavity. Alternatively, retroperitoneal insufflation may be used to maintain the cavity.

A visualization cannula then is used from, e.g., bilateral groin incisions, to form tunnels leading to the retroperitoneal space, for passage of femoral graft limbs. The proximal aortic anastomosis is performed while the aorta is cross-clamped. The femoral limbs of the graft are pulled down through the tunnels and the distal anastomoses are performed via the bilateral groin incisions. This total retroperitoneal approach is applicable to patients with abdominal aortic aneurysms or patients with atherosclerotic aortic occlusive disease.

A double-lumen balloon cannula may be used to perform the blunt dissection of an elongate, non-spherical cavity under visual control. Such a cannula includes a first lumen that accommodates an endoscope therewithin, and a second lumen having an inverted, nonelastomeric, transparent balloon contained therewithin. The balloon is attached to the outer surface of the distal end of the cannula. Thus, as the balloon is being everted, it extends over the distal end of the first lumen to permit passage therethrough of the endoscope for visualization of the tissue adjacent the balloon.

BRIEF DESCRIPTION OF THE DRAWINGS

FIGS. 7A–7G are top cut-away views of the aorta, illustrating the introduction and deployment of the graft therewithin in accordance with the method of the present invention.

DETAILED DESCRIPTION OF THE PREFERRED EMBODIMENTS

The present invention includes an improved method for introducing a graft into a body passageway and apparatus used in practicing the method. In a preferred embodiment, and as described below, the present invention is a method for introducing an aortofemoral bypass graft into the aorta.

Figure 1:
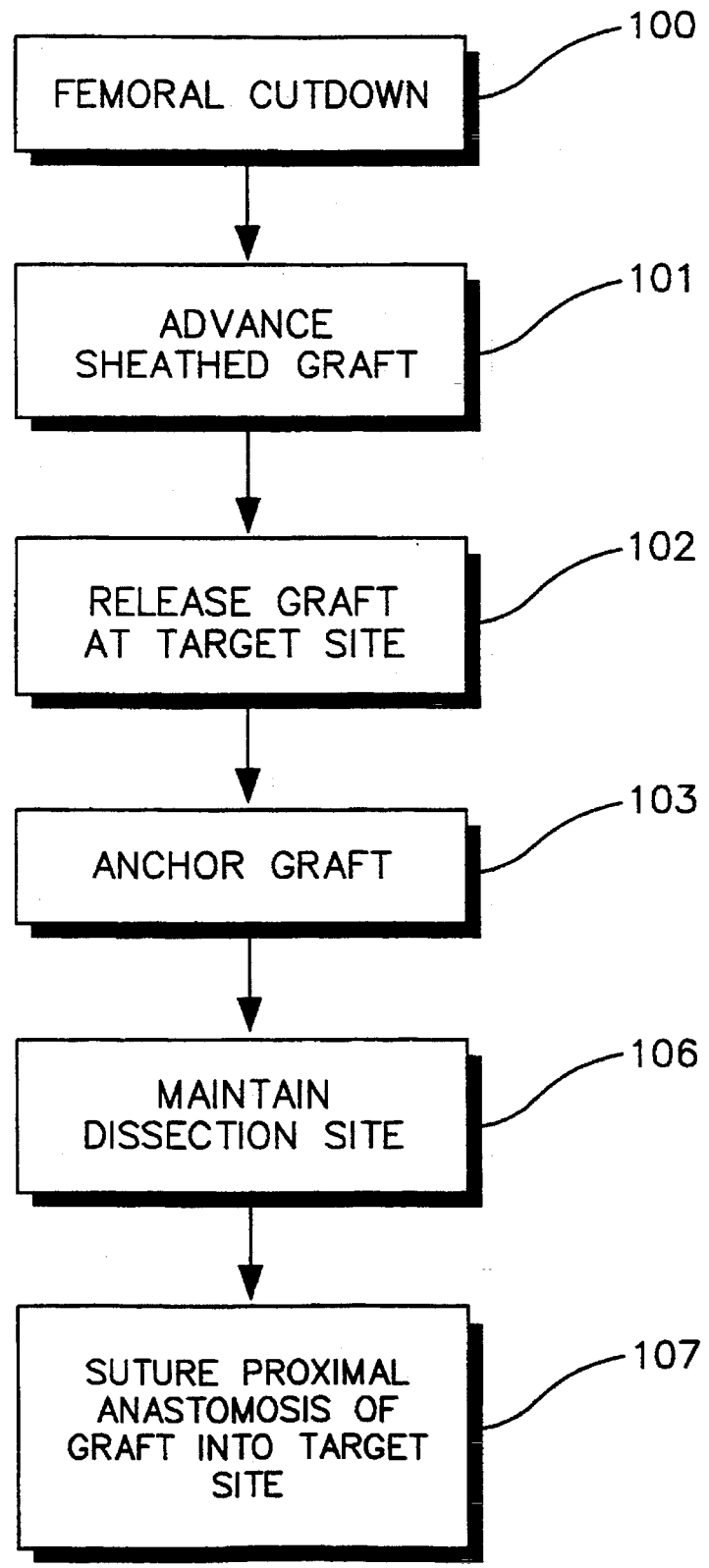
FIG. 1 is a flowchart of one embodiment of the method of the present invention.
Figure 2A:
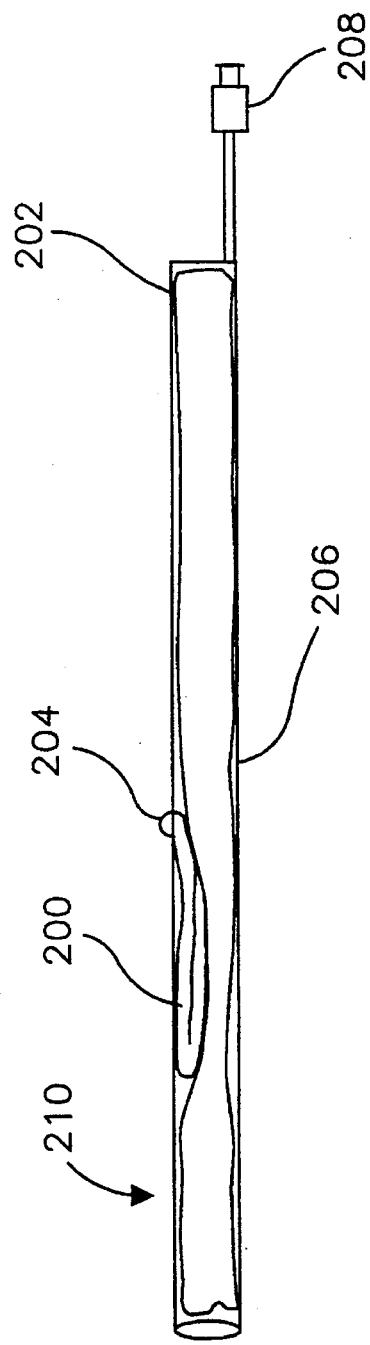
FIG. 2A shows a longitudinal cross-section view of an embodiment of a sheathed graft that may be used in practicing the present method.
Figure 2B:
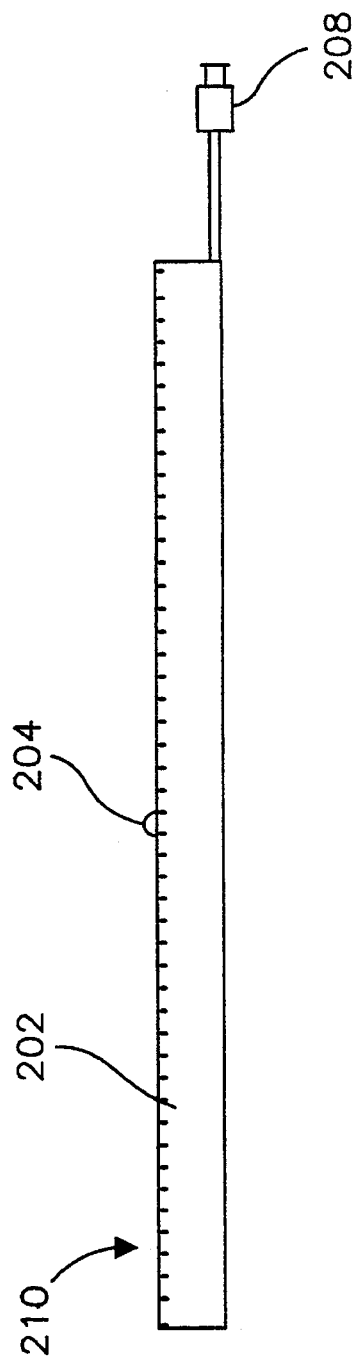
FIG. 2B shows a side elevation view of the sheathed graft of FIG. 2A.
Figure 2C:
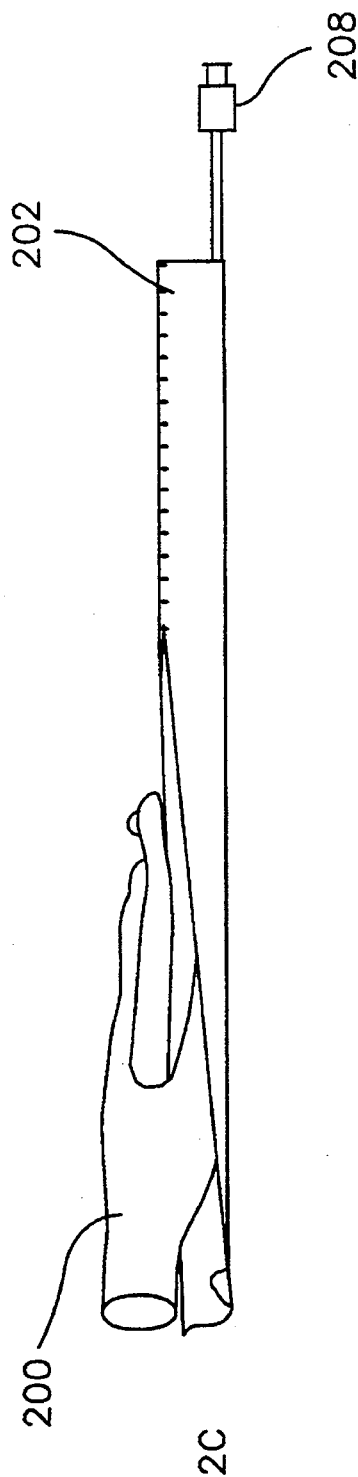
FIG. 2C shows a side perspective view of a graft emerging from the sheath shown in FIGS. 2A and 2B in accordance with the present invention.

A flowchart of one embodiment of the present invention is shown in FIG. 1. In that embodiment, an aortofemoral graft is placed via a femoral artery cutdown 100. Preferably, and as shown in FIGS. 2A through 2C, the graft 200 is encased in a perforated sheath 202 to form a sheathed graft 210.

The graft 200 may be manufactured from tissue, plastics, textiles, and other materials that can be sterilized and that retain shape. Preferably, the graft 200 is formed from a synthetic material such as polytetrafluoroethylene (PTFE, also known as Teflon), or a textile such as Dacron. Alternatively, the graft may be a tissue, such as umbilical vein. PTFE is commercially available from W. L. Gore & Associates, Inc., Naperville, Ill., and the textile is commercially available from Meadox Medicals, Inc., Oakland, N.J. The graft may be made from any suitable materials having good suturability, and which are nonthrombogenic. The graft material preferably also is non-kinking and does not dilate over time. Preferably, the graft 200 is a bifurcated graft constructed of Dacron or Teflon (PTFE or polytetrafluoroethylene), with the proximal half of the graft 200 of approximately 16 mm in diameter, and the distal, femoral limbs of the graft 200 approximately 8 mm in diameter. The sheath 202 may be manufactured from a bioinert plastic, polyethylene, polyurethane, polyvinyl chloride (PVC), polyimide plastic, and the like. In a preferred embodiment, the sheath 202 has a longitudinal perforation added using a cutting die. The sheath 202 may also have a transverse slit approximately halfway along its length.

The femoral limb with an attached loop 204 may be folded in half, and folded back onto the proximal part of the graft 200 at the bifurcation. One half of the sheath 202 encloses the large diameter portion of the graft 200 proximal to the bifurcation, plus the folded femoral graft limb; the other half of the sheath 202 encloses the other femoral graft limb, which remains unfolded. The sheath 202 may be approximately 40–60 cm in length.

The distal end of one femoral limb of the graft 200 has an attached loop 204 that protrudes from an opening in the middle of the sheath 202. This loop 204 is threaded along the length of a previously placed guidewire (not shown) which has been advanced from the first femoral artery incision (arteriotomy), across the aortic bifurcation, and down the contralateral femoral artery, to exit the second femoral arteriotomy. After the graft 200 has been advanced into position in the aorta and released, a bead (not shown) may be crimped onto the guidewire immediately outside the first femoral arteriotomy. The guidewire may be pulled out of the second arteriotomy, with the crimped bead catching the loop 204 and pulling the contralateral femoral limb of the graft 200 down the contralateral femoral artery and out of the second femoral arteriotomy.

An enclosed chamber 206 runs the length of the sheath 202. When this chamber 206 is inflated via an attached inflation port 208, the sheath 202 splits open along the perforation to release the graft 200. The sheath 202 than may be removed from the cavity, or left in place if manufactured from a resorbable material, such as polyglycolic acid. Thus, the present sheathed graft 210 obviates the wire stents or hooks of conventional total endovascular placed grafts. In addition, the initial diameter of the sheathed graft 210 is smaller than conventional endovascular graft inserts since no such stents and hooks are required on the outer surface of the graft of the present invention.

Continuing the present method, the sheathed graft 210 is advanced 101 in a retrograde fashion, from the femoral artery through the iliac artery into the aorta, until it is in position at the target location, preferably against the side of the aorta. The graft 200 then is released 102 from the sheath 202 at the target site, in the manner described above. Specifically, the sheath chamber 206 is inflated with saline or other appropriate fluid until the sheath 202 splits open along the line of perforation to release the graft 200.

The graft 200 is anchored 103 at the target site by suturing the proximal end of the graft 200. In the embodiment wherein the graft 200 is an aortofemoral graft, the anchoring 103 step is achieved by suturing via a retroperitoneal laparoscopic approach. Interrupted sutures may be placed to anchor 103 the proximal end of the graft 200.

Figure 3:
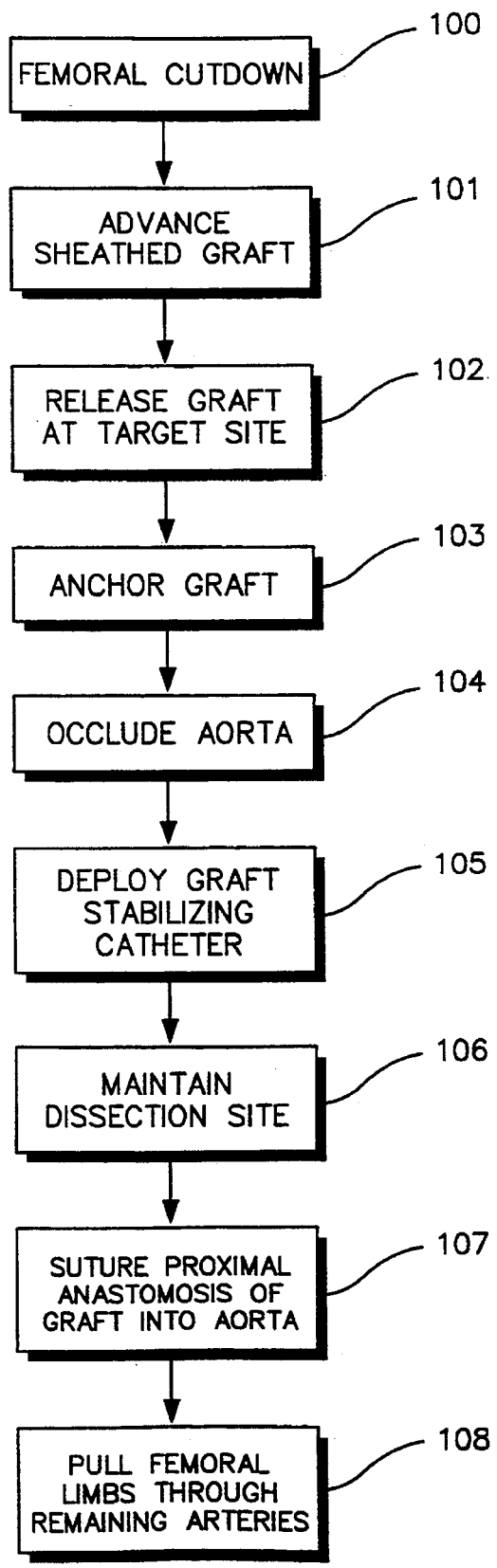
FIG. 3 is a flowchart of an alternative embodiment of the method of the present invention, wherein the graft is an aortofemoral graft.

Once the graft 200 is positioned, the dissection site is maintained 106. This may be achieved in several conventional ways, including using a structural balloon, insufflation, or mechanical structures. In a preferred embodiment, and as outlined in the flowchart shown in FIG. 3, once the graft 200 is anchored 103, the aorta may be occluded 104 by advancing an aortic balloon occlusion catheter 400 proximal to the graft 200 and by inflating the balloon to occlude the aorta. If possible, this occlusion is performed just distal to the origin of the renal arteries, to preserve perfusion to the kidneys. An exemplary occlusion catheter 400 is shown in FIG. 4.

Figure 4:
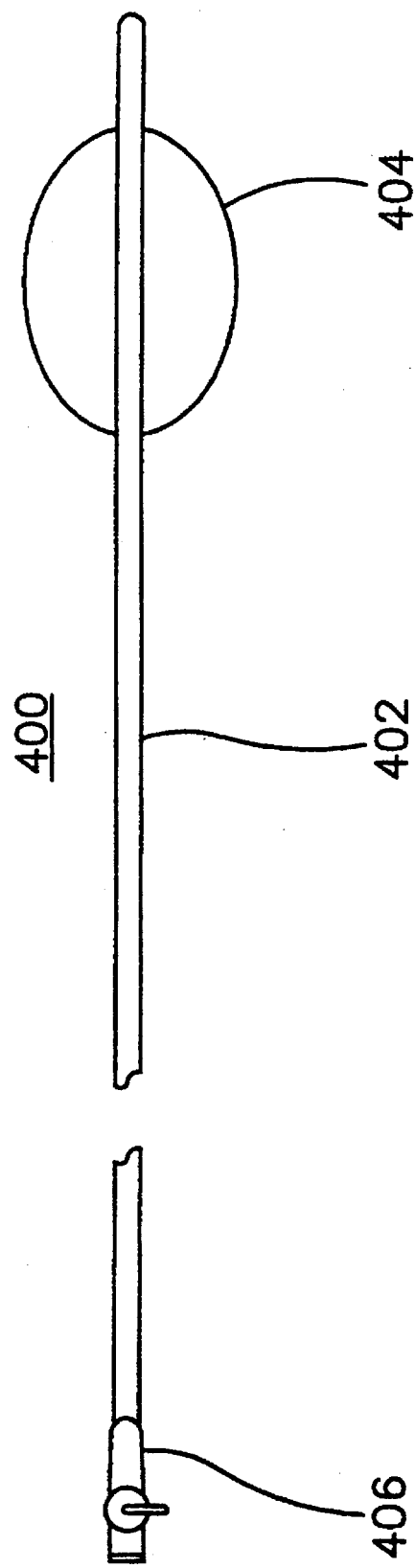
FIG. 4 is a side elevation view of an aortic balloon occlusion catheter that may be used in practicing the present invention.

As shown in FIG. 4, the occlusion catheter 400 may be constructed of a hollow shaft 402 or tube with an elastomeric balloon 404 at one end of the shaft 402 and an inflation port 406 at the other end of the shaft 402. This catheter 400 may be any conventional occluding catheter generally commercially available. In using the illustrated catheter 400, the shaft 402 is introduced to the target site with the balloon 404 collapsed within or tightly surrounding the hollow shaft 402. Once positioned, fluid is introduced via the port 406 into the shaft 402 to inflate the balloon 404.

Once the aorta is occluded 104, the graft stabilizing catheter 500, or other stabilizing catheter system may be deployed 105. Such a catheter 500 is advanced to the proximal end of the graft and deployed to press the graft 200 against the aortic wall. An exemplary graft stabilizing catheter 500 of the type that may be used in practicing the present method is shown in FIGS. 5A through 5C.

Figure 5:
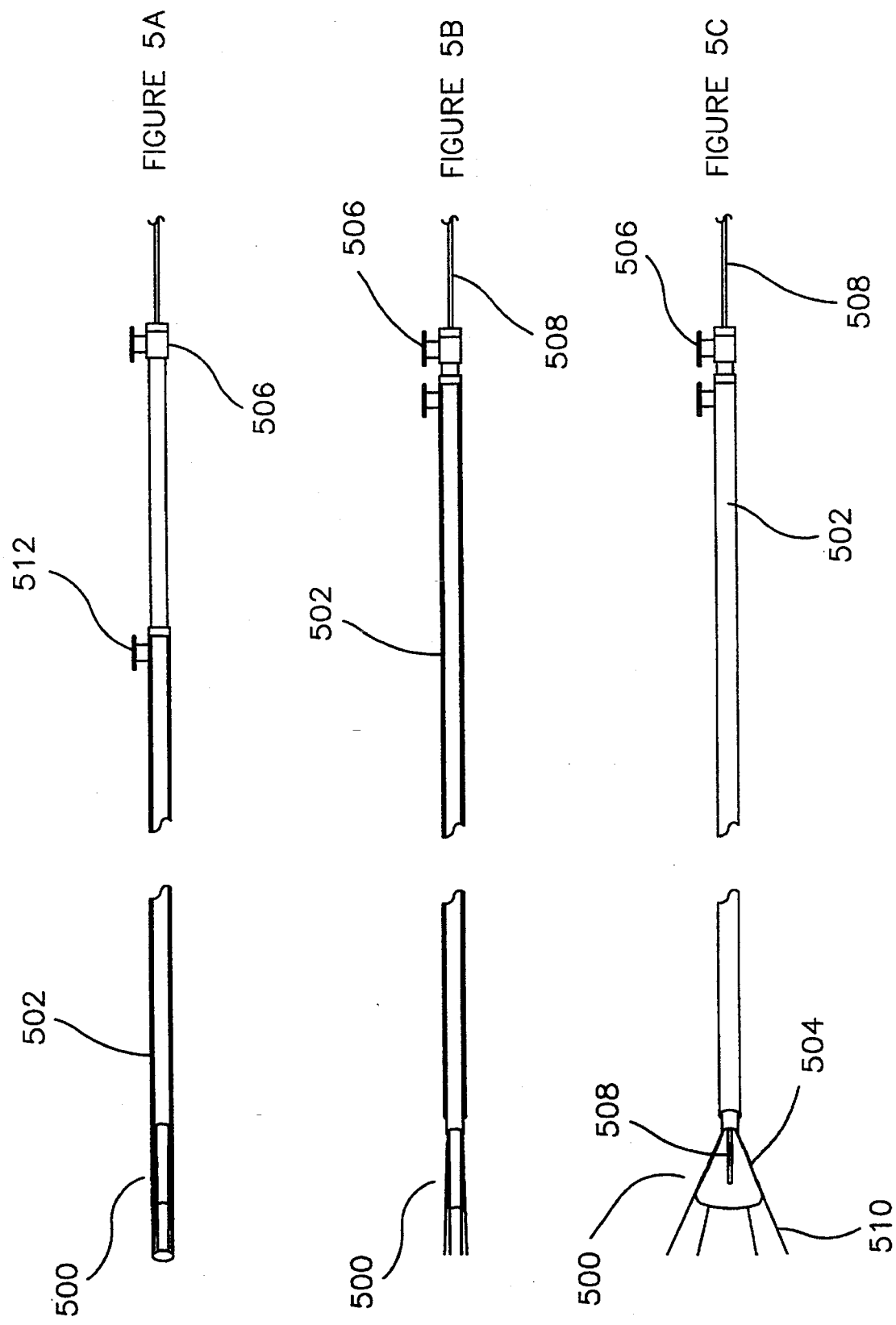
FIG. 5A is a side partial cut-away view of a graft stabilizing catheter that may be used in practicing the present invention.
FIG. 5B is a side cut-away view of the graft stabilizing catheter of FIG. 5A with the sheath drawn back away from the extensions and balloon.
FIG. 5C is a side perspective view of the graft stabilizing catheter of FIGS. 5A and 5B in its fully deployed state.

In that illustrated embodiment, the catheter 500 includes an outer sheath 502 which houses a balloon 504, shown in FIG. 5C in its inflated form. The sheath 502 covers the balloon and several extensions 510 for ease of insertion and advancement through the graft 200. A balloon inflation port 506 is included near the remote end of the catheter 500 in fluid-tight connection to the balloon 504 to facilitate the remote inflation of the balloon 504 to assist in maintaining 106 the dissection site.

Figure 7E:
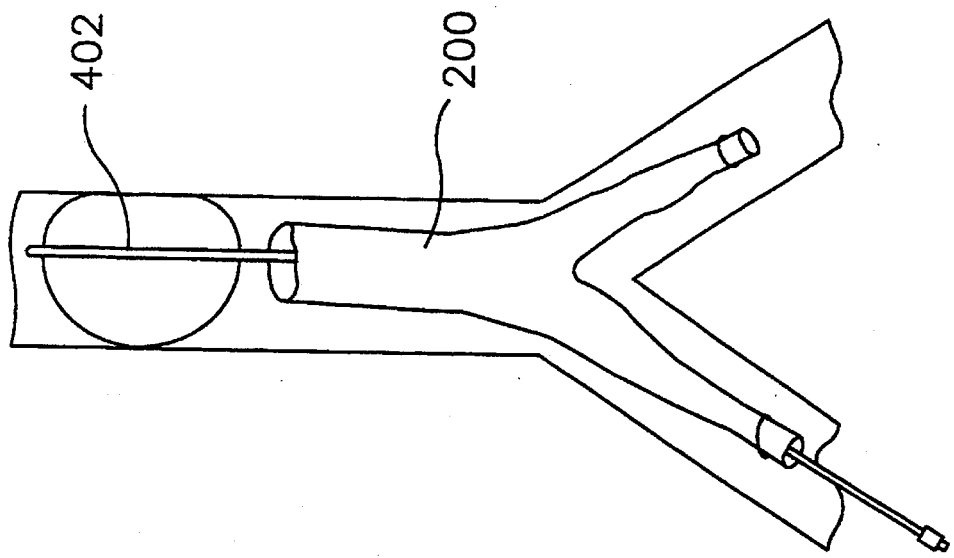

In a preferred embodiment, the catheter 500 includes a fiberoptic endoscope 508 which extends, as shown in FIG. 5C, into the balloon 504 when the balloon 504 is in its deployed, inflated form. Using the endoscope 508, a user may visualize the placement of the catheter 500 at the proximal end of the graft 200, for example, as illustrated in FIG. 7G. In the illustrated embodiment, the catheter 500 includes an irrigation port 512, for flushing the catheter 500 with, e.g., saline. Flushing the catheter 500 with saline clears the graft 200 of blood to allow visualization through the scope 508.

In addition, the illustrated catheter 500 may include several finger-like resilient extensions 510, which splay outward when the balloon 504 is inflated. The extensions 510 are deployed by withdrawing the sheath 502 away from the enclosed extensions 510 which then spring outwardly into a fan-like deployed shape upon inflation of balloon 504, as shown in FIG. 5C. Once deployed, the extensions 510 are visible outside the aorta, assisted by transillumination provided by a fiberoptic light source integral with the endoscope 508.

The extensions 510 may be formed of a stainless steel wire, a nickel-titanium wire, or wire coated with a bioinert coating material, such as polytetrafluoroethylene (Teflon), polyethylene, polyvinyl chloride, or silicone rubber. The balloon may be made of polyethylene, polyethylene terephthalate (PET), polyvinyl chloride, or other generally inelastic materials. The extensions 510 may be attached to the catheter 500, inserted into multiple, symmetrically spaced lumens placed around the central balloon inflation lumen, or they may be bonded to the outside of the catheter 500. The extensions 510 also may be attached to the outer surface of the balloon 504 in a symmetrical fashion, approximately at the midpoint along the length of the extension 510. Thus, each extension 510 is stabilized at two points, at the proximal end and at its midportion, allowing the distal end of the extension to pivot outward upon inflation of balloon 504.

Once the graft 200 is properly positioned and maintained in the aorta or at the target site, the proximal end of the graft is sutured 107 to the target site, or into the aorta. Placement of interrupted sutures preferably is accomplished from the outside of the aorta, via the retroperitoneal route. The fiberoptic scope 508 in the stabilizing catheter 500 allows evaluation of suture placement from the inside of the graft 200.

The aortobifemoral graft 200 typically includes two femoral limbs. If the graft 200 is advanced via the right femoral artery, as illustrated in FIG. 7A, the left limb of the graft 200 must be pulled 108 down the left iliac and femoral arteries. This may be accomplished by the prior introduction of a catheter 700, including a guidewire 702, via the right femoral artery, which then passes over the aortic bifurcation and down the left femoral artery, as shown in FIG. 7B.

The distal end of the left femoral limb of the aortobifemoral graft may include a small loop 704 that is threaded over the guidewire 702, as the graft 200 is advanced into the aorta. A small bead 706 may be crimped onto the guidewire 702 so that passage of the guidewire 702 out of an incision in the left femoral artery facilitates manually pulling the left femoral limb of the graft 200 into the left femoral artery and out the incision, following the bead 706.

Figure 7D:
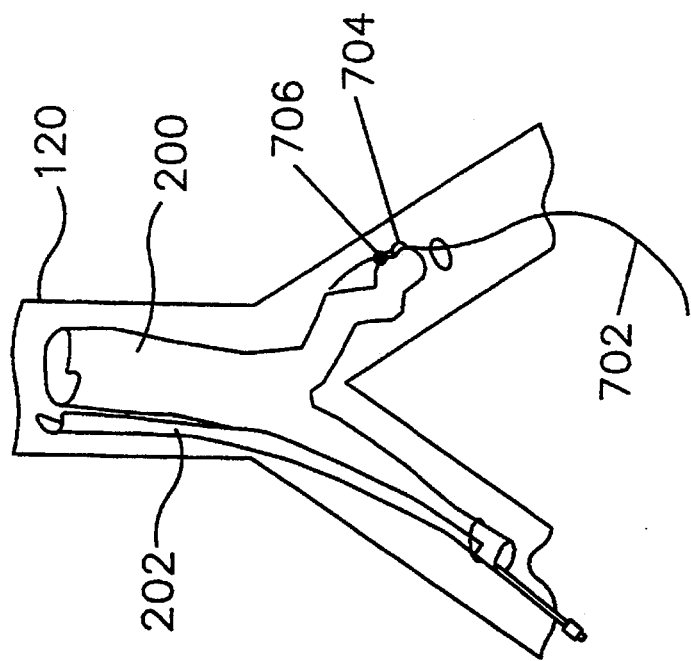
Figure 7G:
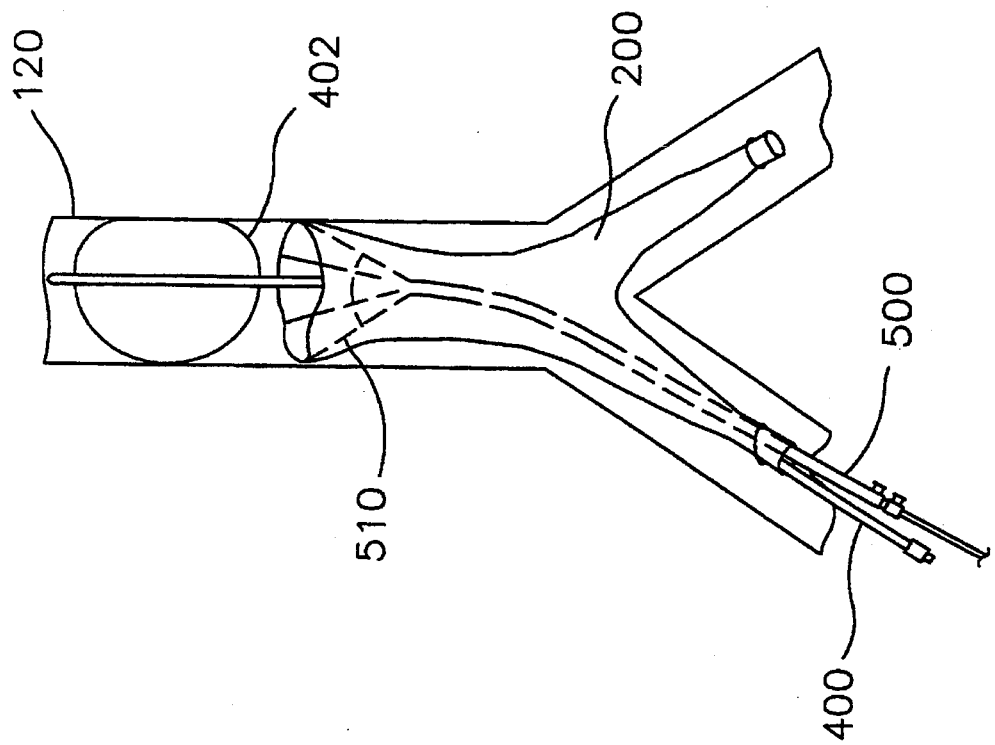

The present method is described further with reference to FIGS. 7D and 7G. As illustrated, once the sheathed graft 210 is in position, the sheath 202 is split open at the perforation to release the graft 200 into position in the aorta 120. The aortic occlusion balloon 400 then is introduced through the positioned graft, as shown in FIG. 7E, and the balloon 402 is distended to occlude 104 the aorta above the graft site.

Figure 7F:
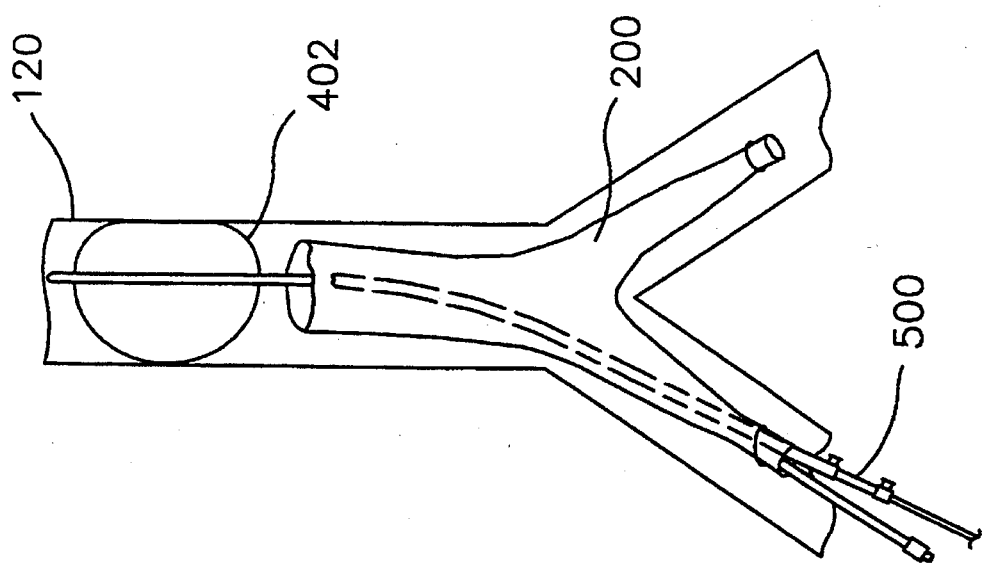

The stabilizing catheter 500 then is introduced into the graft 200, as shown in FIG. 7F, the sheath 502 retracted, and the balloon 504 inflated, to deploy the extensions 510 within the graft 200, as shown in FIG. 7G. The graft 200 then may be sutured 107 into place. As a final step, the femoral limbs of the graft 200 are pulled 108 through the remaining arteries, as shown in FIGS. 7D, 7E, 7F, and 7G, for suturing the graft into place.

Figure 6:
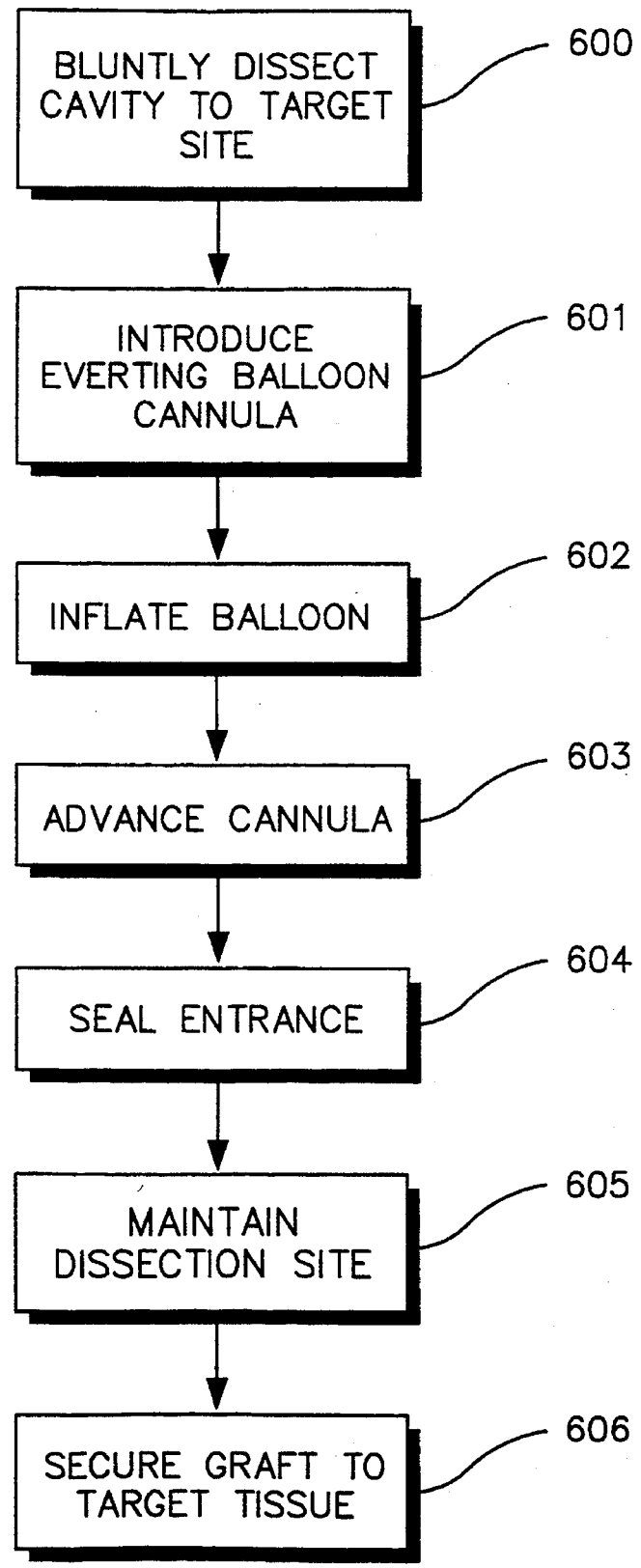
FIG. 6 is a flowchart illustrating an alternative embodiment of the method of the present invention.

In another embodiment of the present invention, and as shown in the flowchart of FIG. 6, a blunt dissection cannula 800, is used to bluntly dissect 600 a cavity extending from an initial incision to the target graft site. In a preferred embodiment, a 15 mm incision is made in the left flank, approximately 2 cm above the iliac crest in the anterior axillary line. Separate groin incisions may be made to isolate the common femoral artery on both sides.

Figure 8A:
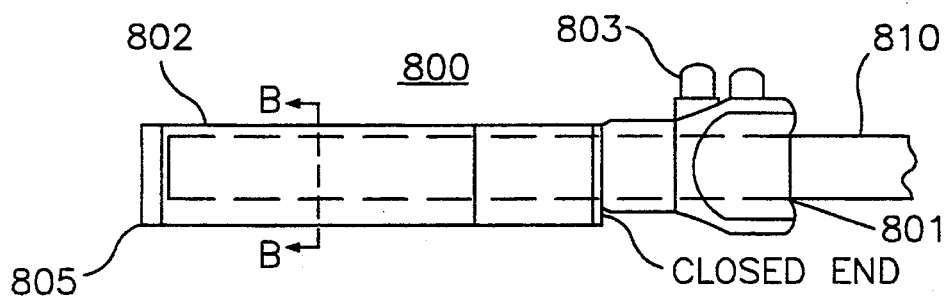
FIG. 8A shows a side elevation view of an embodiment of an everting balloon cannula that may be used in practicing the present method.
Figure 8B:
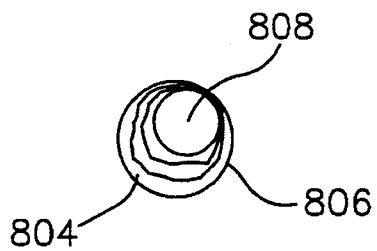
FIG. 8B shows in cross-section the cannula of FIG. 8A taken along lines B—B of that figure.
Figure 8D:
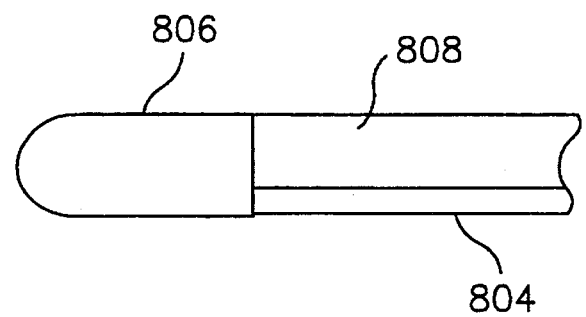
FIG. 8D is a longitudinal cross-section of the cannula of FIG. 8C, showing the balloon in its active, everted position.

A blunt dissection cannula 800 that may be used in practicing the present invention is shown in FIGS. 8A through 8D. In that illustrated embodiment, the cannula 800 includes an inverted inelastic balloon 806 folded within a first lumen, and an endoscope 810 within a second lumen. Once the cannula 800 is positioned, the balloon 806 is inflated via a pressure fitting 803 to extend the balloon 806 from the end of the cannula, as shown in FIG. 8D and bluntly dissect an elongated tissue plane. The endoscope 810 may be inserted through end 805 that includes a gas-tight sliding seal to facilitate visualizing the dissection process from within the inflated balloon 806 as the cannula 800 is advanced.

Blunt finger dissection 600 and muscle spreading result in a plane down to the peritoneum. An everting balloon cannula 800, preferably of the type shown in FIGS. 8A through 8D, then is introduced 601 into the incision and pointed inferiorly. The balloon 806 of the everting cannula 800 is inflated 602 and the balloon 806 everts 603 to create a cavity along the target site, e.g., the aorta. The balloon 806 then is deflated and the cannula 800 removed prior to introduction of a trocar. After dissection, a blunt tip trocar with a sealing balloon and a movable foam cuff may be used to seal 604 the entrance tract and allow maintenance 605 of the dissected space for subsequent instrument insertion and manipulation via insufflation. A conventional blunt tip trocar may be used, such as ones commercially available from Origin Medsystems, Inc. (Menlo Park, Calif.).

Figure 9:
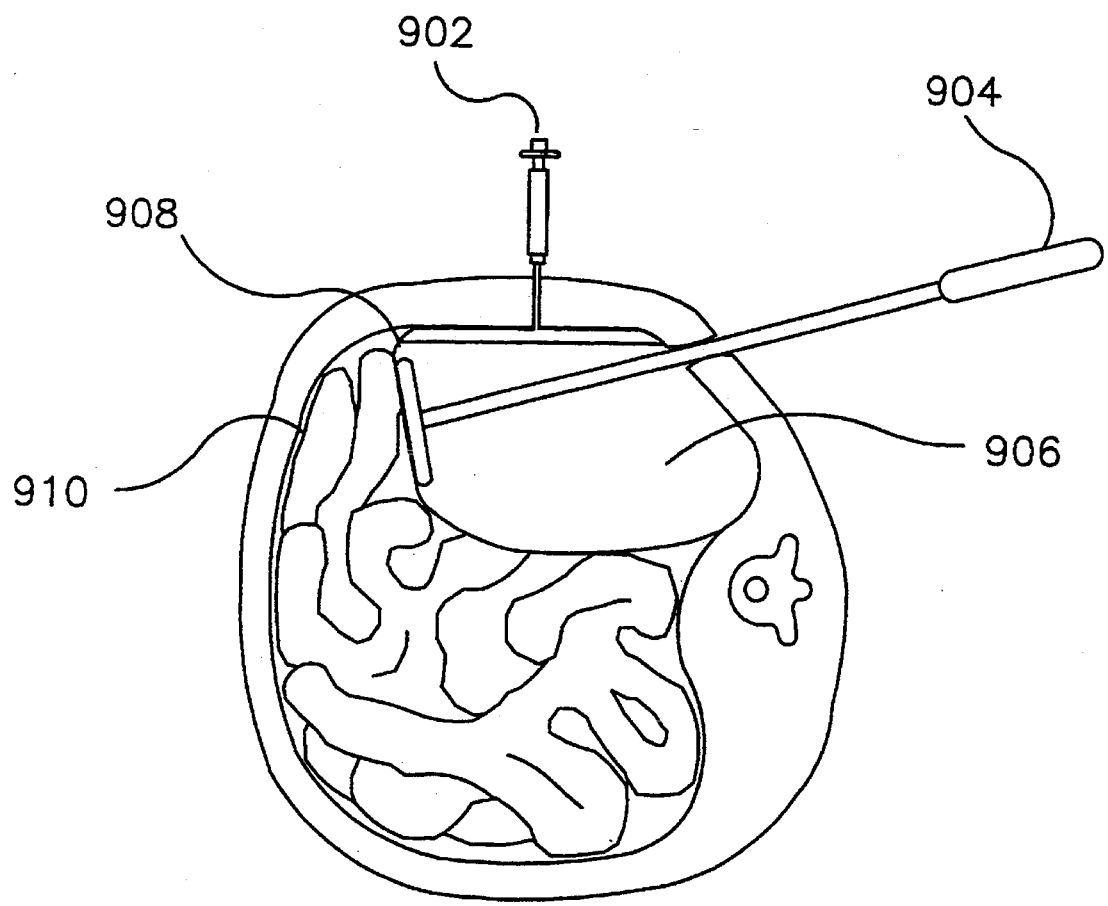
FIG. 9 is a cross-sectional view of a retroperitoneal cavity with a balloon retractor and a fan retractor in position in accordance with the present invention.

Mechanical support may allow maintenance 605 of the dissected space without the need for a blunt tip trocar or insufflation. The mechanical support may include a fan retractor 902, attached to a mechanical arm (not shown) used in conjunction with a separate small mechanical or balloon retractor 904, as shown in FIG. 9. In that illustrated embodiment, the fan retractor 902 is introduced into the retroperitoneal cavity 906 then activated to maintain that cavity 906 in an expanded manner. The balloon retractor 904 is introduced into the cavity 906 and used to apply pressure against the peritoneum 908 and thus against the bowel 910.

Figure 10A:
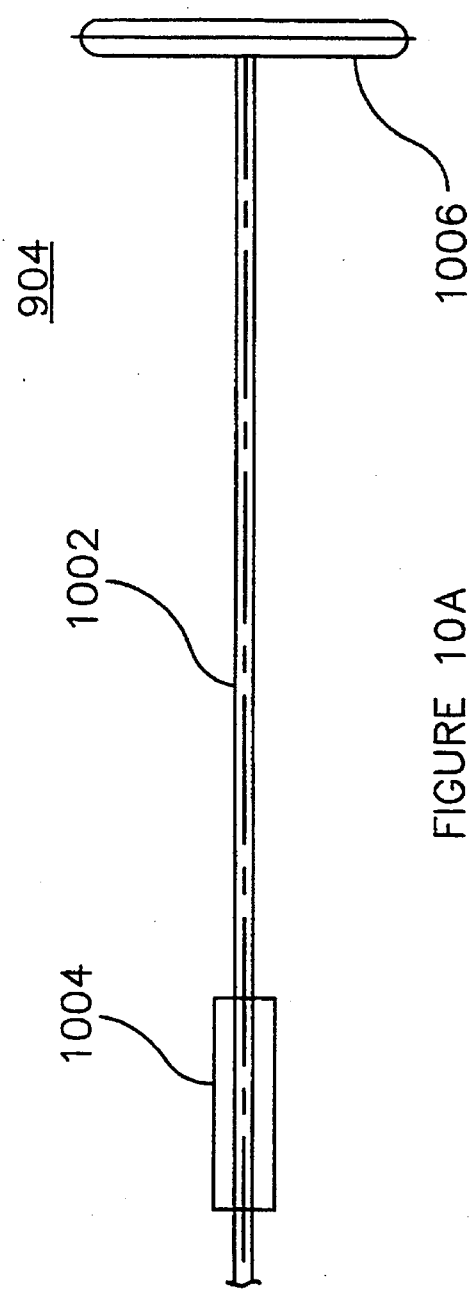
FIG. 10A is a top plan view of a laparoscopic oval balloon retractor that may be used in practicing the present invention.
Figure 10B:
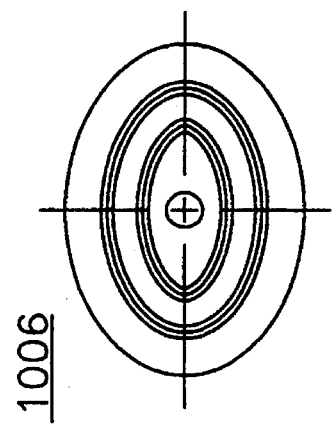
FIG. 10B is a front plan view of the oval balloon of the retractor shown in FIG. 10A.

FIG. 10A shows a top plan view of an exemplary laparoscopic oval balloon retractor 904 of the type that may be used in practicing the present invention. As shown, the retractor 904 includes a substantially rigid, tubular shaft 1002, with an attached handle 1004 at one end and a flexible, inflated, oval balloon 1006 at the other end. The balloon 1006 is shown in front plan view in FIG. 10B.

Alternatively, the dissecting balloon cannula 800 may be a structural type balloon with operating windows for access to the infrarenal aorta and the aortic bifurcation. Thus, the dissected space may be maintained 605 in a manner similar to that described above.

Figure 11:
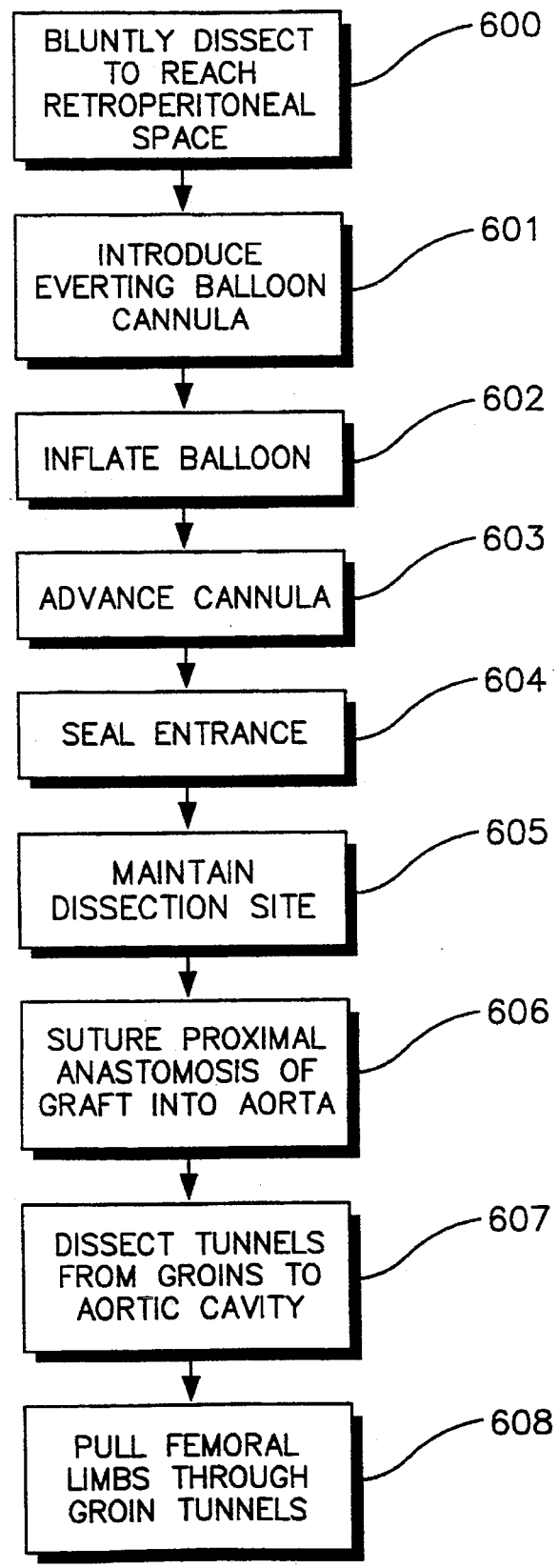
FIG. 11 is a flowchart of an alternative embodiment of the method of FIG. 6.

Once the dissection site is established, the graft 200 may be secured 606 in place, preferably by suturing the graft 200. In a preferred embodiment, and as shown in the flowchart of FIG. 11, the proximal end of the graft may be sutured 606 into the aorta and may be performed via the retroperitoneal cavity. Tunnels then may be dissected 607 from the groin incisions to the retroperitoneal cavity, and the femoral limbs of the graft pulled 608 through the dissected tunnels. In that embodiment, the distal anastomoses are performed via the groin incisions.

Figure 8C:
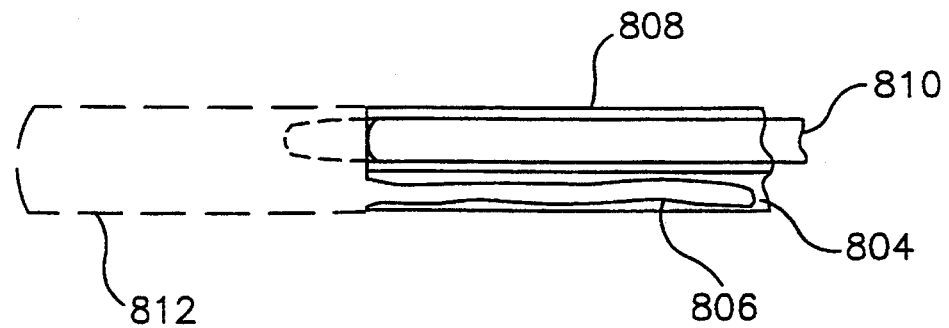
FIG. 8C shows the cannula of FIG. 8A in longitudinal cross-section, showing the balloon in its inactive, inverted position within the balloon lumen.

FIGS. 8A–8C show an embodiment of the dissection cannula 800 of the present invention. This illustrated cannula is described in detail in U.S. patent application Ser. No. 269,666, filed 1 Jul. 1994, and entitled "Everting Cannula Apparatus and Method", which application is incorporated by reference herein in its entirety.

The cannula 800 includes an elongated, tubular member 802 having one lumen 804 for containing an inverted balloon 806 and another lumen 808 for supporting an endoscope 810 therein as shown in cross-section in FIGS. 8B and 8C. In other embodiments, the cannula 800 may include additional lumens, such as a lumen through which a guide-wire may be passed.

An elliptical, nonelastic balloon 806 is inverted into lumen 804 prior to introduction of the cannula 800 to the dissection site. The balloon 806 is attached to the outer edges of the distal end of the cannula 800 to ensure that the balloon 806, when in its everted, inflated state (shown in FIG. 8D), extends outwardly from the distal end of the cannula 800 and completely encloses that end of the cannula 800.

As shown in FIG. 8A, the proximal end of the cannula 800 preferably is sealed. In addition, a conventional sliding pressure seal 801 is provided around an endoscope inserted into the lumen 808. This enables a positive pressure to be established within the balloon lumen 804 upon activation of the cannula 800 at the dissection site. When a positive pressure is established within that lumen 804, the inverted balloon shown in FIG. 8C becomes everted and extended, as shown in FIG. 8D. The positive pressure necessary to evert the balloon 806 may be produced by air or fluid introduced into the lumen 804 via a pressure fitting 803 at the proximal end of the cannula 800 which communicates with the balloon lumen 804 to receive a source of air or fluid under pressure, for example from a manually operable syringe.

The illustrated cannula 800 also includes a second lumen 808 for housing an endoscope 810 therewithin. The size of the lumen 808 depends on the diameter of the endoscope 810 to be introduced therewithin. A preferred endoscope 810 having a tubular diameter of about 10 mm is commercially available from Karl Storz Endoscopy America, Inc.

What is claimed is:

1. A method for reconstruction of target tissue using a sheathed graft that is encased in an inelastic perforated casing and that includes an enclosed expandable chamber extending along the graft, using a stabilizing catheter having a plurality of selectively deployable extensions at one end thereof, the method comprising the steps of:

introducing the sheathed graft via an introduction site to position the sheathed graft at a proximal part of the target tissue;

elevating fluid pressure within the chamber to expand the chamber sufficiently to split the perforated casing for releasing the graft from the perforated casing;

deploying the extensions of the stabilizing catheter at a proximal part of the graft to press the graft adjacent the target tissue to stabilize the graft at the target tissue; and securing the graft to the target tissue.

2. The method of claim 1, wherein the stabilizing catheter includes at least a first lumen with an endoscope slidably positioned therewithin and a second lumen with a selectively inflatable balloon therewithin, and the extensions are slidably disposed in a sheath, the method further comprising the step of deploying the extensions in response to at least a partial removal of the sheath and inflation of the balloon, to hold the graft within the target tissue to stabilize the graft as it is being secured to the target tissue.

3. A method for reconstruction of target tissue of a body, using a dissection balloon cannula including an elongated tube element and having a plurality of lumina including a distal blunt end and a proximal closed end with an inverted balloon disposed in a first one of the lumina and capable of being everted in response to gas or fluid under pressure applied thereto, and with a second one of the lumina disposed to receive a laparoscope therein, for visualizing the tissue in the elongated cavity through the balloon as the balloon is everted; the method comprising the steps of:

positioning the cannula at a predetermined location within a passageway to dissect an elongated cavity in tissue planes distal to the tube element;

pressurizing the balloon to evert forward from the cannula to dissect a cavity along the target tissue using the dissection balloon cannula introduced via an incision made at a predetermined location on the body;

advancing the laparoscope within the second lumen for visualizing the dissection of tissue from within and through the balloon;

maintaining the cavity;

positioning the graft adjacent to the target tissue via the cavity; and securing the graft to the target tissue.

4. The method of claim 3, wherein the target tissue comprises aortic tissue, and the step of positioning the graft comprises positioning the graft adjacent to the aortic tissue.

5. The method of claim 4, wherein the predetermined location comprises a left flank.

6. The method of claim 4, further comprising the step of, prior to the dissecting step, blunt dissecting to develop a tissue plane in retroperitoneal tissue.

7. The method of claim 4, wherein the maintaining step further comprises introducing a blunt tip trocar, having a sealing balloon and a movable foam cuff introduced via the incision and into the cavity.

8. The method of claim 7, further comprising the step of, after introducing the blunt tip trocar, sealing the incision by inflating the sealing balloon and compressing the incision between the sealing balloon and the movable foam cuff.

9. The method of claim 3, wherein the step of maintaining the cavity comprises insufflating the cavity by introducing a gas therewithin.

10. The method of claim 3, wherein the step of maintaining the cavity comprises using at least one mechanical support device positioned within the cavity and deployed to support the cavity.

11. A method for reconstruction of aortic tissue, using a sheathed graft having a loop element attached thereto and being encased in an inelastic perforated casing, and using a stabilizing catheter having a plurality of selectively deployable extensions at one of thereof, the method comprising the steps of:

introducing the sheathed graft via an introduction site for advancing the sheathed graft into position at a proximal part of the aortic tissue via one femoral artery;

releasing the graft from the perforated casing;

inserting a balloon occlusion catheter, having a selectively inflatable balloon, through the graft;

selectively inflating the balloon to occlude the aorta;

deploying the extensions of the stabilizing catheter at a proximal part of the graft to press the graft adjacent the aortic tissue to stabilize the graft at the aortic tissue;

securing the graft to the aortic tissue;

introducing a guide wire through the loop element into the femoral arteries and iliac arteries; and pulling a limb of the graft down iliac arteries and femoral arteries opposite the introduction site.

12. The method of claim 11, wherein the guidewire includes a bead attached at a predetermined location along the guidewire, the bead having a diameter sufficient to pass through an aperture in one of the femoral arteries but insufficient to pass through the loop, and wherein the step of introducing a guidewire further comprises introducing the guidewire through the loop to secure the graft at the bead, and the method further comprises pulling the guidewire through the introduction site in one of the femoral arteries to pull the graft secured at the bead through the femoral artery on the side opposite the introduction site.

* * * * *